US006650939B2

United States Patent
Taepke, II et al.

(10) Patent No.: US 6,650,939 B2
(45) Date of Patent: Nov. 18, 2003

(54) UNIVERSAL INTERFACE FOR IMPLANTABLE MEDICAL DEVICE DATA MANAGEMENT

(75) Inventors: Robert T. Taepke, II, Coon Rapids, MN (US); Jonathan P. Roberts, Shoreview, MN (US); Tom D. Bennett, Shoreview, MN (US); Robert C. Beck, St. Paul, MN (US); Richard J. Shaw, St. Francis, MN (US); D. Curtis Deno, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 298 days.

(21) Appl. No.: 09/809,914

(22) Filed: Mar. 16, 2001

(65) Prior Publication Data

US 2001/0039437 A1 Nov. 8, 2001

Related U.S. Application Data

(60) Provisional application No. 60/190,465, filed on Mar. 17, 2000.

(51) Int. Cl.[7] .................................................. A61N 1/30
(52) U.S. Cl. .............................. 607/27; 600/486; 607/6; 607/9; 607/112
(58) Field of Search ..................... 607/6, 27, 122, 607/9, 31, 2, 17, 40, 30, 115, 5; 600/486

(56) References Cited

U.S. PATENT DOCUMENTS

| 4,791,931 | A |   | 12/1988 | Slate          | 128/419 |
|-----------|---|---|---------|----------------|---------|
| 5,330,505 | A |   | 7/1994  | Cohen          | 607/6   |
| 5,368,040 | A |   | 11/1994 | Carney         | 128/700 |
| 5,535,752 | A |   | 7/1996  | Halperin et al.| 128/670 |
| 5,564,434 | A |   | 10/1996 | Halperin et al.| 127/748 |
| 6,024,704 | A | * | 2/2000  | Meador et al.  | 600/486 |
| 6,152,885 | A |   | 11/2000 | Taepke         | 600/561 |
| 6,155,267 | A |   | 12/2000 | Nelson         | 128/899 |

* cited by examiner

Primary Examiner—Hieu T. Vo
Assistant Examiner—Johnny H. Hoang
(74) Attorney, Agent, or Firm—Girma Wolde-Michael; Daniel G. Chapik (57) ABSTRACT

Medical device data is transferred using a universal adaptor between an implanted medical device and hospital monitoring systems. The universal adaptor is an interface compatible with various built-in hospital monitoring network comprised of equipment from a variety of manufacturers. The universal adaptor includes a telemetry circuitry, a calibration system for atmospheric pressure and an analog interface. The calibration system relates to barometric correction and includes an external pressure reference system.

18 Claims, 4 Drawing Sheets

UNIVERSAL INTERFACE FOR IMPLANTABLE MEDICAL DEVICE DATA MANAGEMENT

CROSS REFERENCE TO RELATED APPLICATIONS

The present application claims the benefit of earlier filed provisional application 60/190,465, filed on Mar. 17, 2000, and incorporated herein by reference in its entirety.

FIELD OF THE INVENTION

The present invention relates to implantable hemodynamic monitors (IHMs). Specifically, the invention relates to a device that interfaces with various hospital monitoring systems and various equipments fabricated by different manufacturers to transfer data from the IHMs to hospital monitoring systems. More specifically, the invention pertains to a data management interface system that is compatible with various models of monitoring equipment built by different manufacturers. Further, the invention relates to a data management system that connects IHMs and a remote monitoring system to transfer the patient's medical data and information to an expert data station center where expert systems and personnel are stationed to monitor patients located in various hospital rooms and/or wards.

BACKGROUND OF THE INVENTION

Health care professionals are fully aware of the need to monitor, on a frequent or continuous basis, the vital signs associated with hospitalized patients, particularly those who are seriously and chronically ill. Virtually every hospitalized patient requires periodic measurement and logging of blood pressure, temperature, pulse rate, etc. This type of monitoring has typically been performed by having a health care worker periodically visit the bedside of the patient and measuring and/or observing the patient's vital signs using dedicated equipment that is either hooked up to the patient or brought into the patient's room. Current monitoring procedures are not ideally cost effective because of being highly labor intensive. Moreover, if an invasive procedure is used, the need to continuously monitor the patient becomes critical because of the associated risk.

To alleviate such concerns, hospitals have adopted new and improved patient monitoring methods and processes. The two most frequently used are 1) intensive care wards and 2) "stepped down" care or "monitored bed" wards. In an intensive care ward, physicians and staff check the patient frequently and directly observe pressure signals on the bedside monitor. This bedside monitor is usually connected, via hardwire, analog or digital, to a central nurses'station where the pressure can be continuously watched or observed. These readings can also be documented by placing them in digital storage such as a disk, for example, or printed on paper for inclusion in the patient's file. A "stepped down" ward is a less intensive setting in which the patient can be monitored as described above. In either case, the pressure monitors may be hardwired or connected via RF to central monitoring stations.

A great many implantable medical devices (IMDs) are currently used for cardiac monitoring and/or therapy. Generally, these devices include sensors located in a blood vessel or heart chamber and coupled to an implantable monitor or therapy delivery device. For example, IMDs include implantable heart monitors, therapy delivery devices such as pacemakers, cardioverter/defibrillators, cardiomyostimulators, ischemia treatment devices, and drug delivery devices. Typically, these cardiac systems include electrodes for sensing and sense amplifiers for recording and/or deriving sensed event signals from the intracardiac electrogram (EGM). In current cardiac IMDs that provide a therapy, the sensed event signals are used to control the delivery of the therapy in accordance with an operating algorithm. Selected EGM signal segments and sensed event histogram data or the like are stored in internal RAM for data telemetry via an external programmer at a later time.

Efforts have also been underway for many years to develop implantable physiologic signal transducers and sensors for temporary or chronic use in a body organ or vessel usable with such IHMs for monitoring a physiologic condition other than, or in addition to the disease state that is to be controlled by a therapy delivered by the IMD. A comprehensive listing of implantable therapy delivery devices are disclosed in conjunction with implantable sensors for sensing a wide variety of cardiac physiologic signals in U.S. Pat. No. 5,330,505, incorporated herein in its entirety by reference.

Typically, an IHM measures right ventricular (RV) blood pressure that stems from changes in cardiac output that may be caused by a cardiac failure, ventricular tachycardia, flutter, or fibrillation. These variations may reflect a change in the body's need for oxygenated blood. An IHM may also measure temperature, a compensatory variable. Measuring temperature is used in these situations to correct for potential erroneous judgment stemming from changes in RV pressure resulting from body temperature changes. Temperature measurements have been used informally to identify disease processes not attributable to heart failure, such as the flu, which might be confused with changes in pressure that otherwise might be attributable to heart failure.

For example, as disclosed in U.S. Pat. No. 6,024,704 issued to Meador et al, monitoring of a substantial drop in blood pressure in a heart chamber, particularly the right ventricle, alone or in conjunction with an accelerated or chaotic EGM, is considered as an indicator of fibrillation or tachycardia sufficient to trigger automatic delivery of defibrillation or cardioversion shock. More recently, it has been proposed to monitor the changes in the blood pressure type (dP/dt) by comparing the absolute blood pressure rise and fall rates (dP/dt) that accompany the normal heart contraction and relaxation to those that occur during high rate tachycardia, flutter, or fibrillation.

A number of cardiac pacing systems and algorithms for processing the monitored mean blood pressure or monitored dP/dt have been proposed and, in some instances employed clinically, for treating bradycardia. Such systems and algorithms are designed to sense and respond to changes in mean blood pressure or dP/dt, to change the cardiac pacing rate (rate responsive pacing) between an upper and a lower pacing rate limit in order to control cardiac output.

Such IHMs, blood pressure, and temperature sensors that derive absolute blood pressure signals and temperature signals are disclosed in commonly assigned U.S. Pat. Nos. 5,368,040, 5,535,752 and 5,564,434, and in U.S. Pat. No. 4,791,931 all incorporated by reference herein. The MEDTRONIC® Chronicle® Implantable Hemodynamic Monitor (IHM), disclosed in U.S. Pat. Nos. 6,024,704 and 6,152,885 both incorporated herein by reference in their totality, employs the leads and circuitry disclosed in the above-incorporated, commonly assigned, '752 and '434 patents to record absolute blood pressure values for certain intervals. The recorded data is transmitted to a programmer preferably under the control of a physician in an uplink telemetry transmission from the IHM. As is well known in the art, a telemetry session is initiated by a downlink telemetry transmission from the programmer's radio frequency (RF) head and receipt of an interrogation command by the IHM.

Thus, in accordance with the disclosures in the '704 and '885 patents, an IHM for deriving an absolute pressure signal value is coupled and compared with a barometric reference signal using implantable physiologic sensor(s) to determine a resultant nonabsolute cardiac pressure signal values for storage and transmission. Further, the patents ('704 and '885) disclose a system of calibration of the reference pressure and/or temperature sensor in relation to an external, calibrated, barometric pressure and/or body temperature sensor. This system may be implemented to interlace digital signal values (related to pulmonary artery diastolic pressures) with the primary cardiac pressure signal values derived from the right ventricle, as disclosed in U.S. Pat. No. 6,155,267 incorporated herein by reference.

In accordance with the present invention, an IHM may be implanted in a rather broadly defined group of patients. The requirements for implant include symptomatic heart failure of at least 3 months duration. These are the sickest patients who consume a large percentage of health care dollars. They require frequent hospitalization and frequent catheterizations—both of which require large expenditures in resources and money, and pose great risk to the patient. When implanted, the IHM is used to monitor the progression of a patient's disease and tune up medications as needed. The medical objective for these patients is to manage them non-invasively within a less intensive clinical setting or as outpatients in a home setting. With trans-telephonic monitoring from their home, they would perhaps require even fewer clinic visits.

Generally, these patients frequently require hospital visits, even if placed in out-of-hospital settings. Nearly 70% of patients may need hospitalization in the first year of medical care for heart failure. Higher percentages of hospitalizations may be encountered post-implant. The present invention provides significant cost reductions while enhancing the quality of care of heart failure patients, both in the hospital and at home.

Heart failure is a progressive disease and, while treatment slows the progression, the disease is not currently curable. Once the patients are hospitalized, there is still no known method or device, to continuously monitor them, except to use a dedicated IHM programmer that must be implanted to gain access to the pressure waveform. Only trained clinicians can currently uplink the data and this is available only when such medical personnel are present. The dedicated programmer (one per bed) is also expensive. In addition, the programming head must be held over the IHM, thus making it impracticable for continuous monitoring of the patients. The present invention enables uninterrupted continuous monitoring by nursing staff or healthcare providers via standard equipment which is commonly available in hospitals and care centers.

SUMMARY OF THE INVENTION

The present invention provides an interface that enables the transfer of a hospital patient's medical data to any of the existing monitoring systems fabricated by over forty different manufacturers. These monitoring systems, in turn, are connected via telemetry to a remote data center, to display medical data in real time to expert personnel (e.g., trained nurses, technicians, etc.) within a hospital. Although the IHM system used to collect data that is passed through the interface described herein is currently limited to the measurement of cardiac pressure, IHM devices may be adapted to detect and transmit other physiologic signals (such as Oxygen saturation, pulmonary artery diastolic pressure, systolic pressure, temperature, etc,) via the interface described herein.

Transferring real-time signals from the IHM into various bedside monitors that are manufactured by various manufacturers, would normally be difficult because of compatibility across the various monitors. Transmitting signals from the IHM on a universal basis would normally require a significant investment in acquiring the external bedside monitor from each manufacturer and communications protocols to comply with various standards. The task is made somewhat easier because the IHM typically measures cardiac pressure at this time. There are many available commercial bedside monitors that use industry-standard extracorporeal pressure transducers. For example, there are over one hundred different models from over forty separate manufacturers that are compatible with the Abbot Critical Care's Transpac IV transducer.

Figure 4:
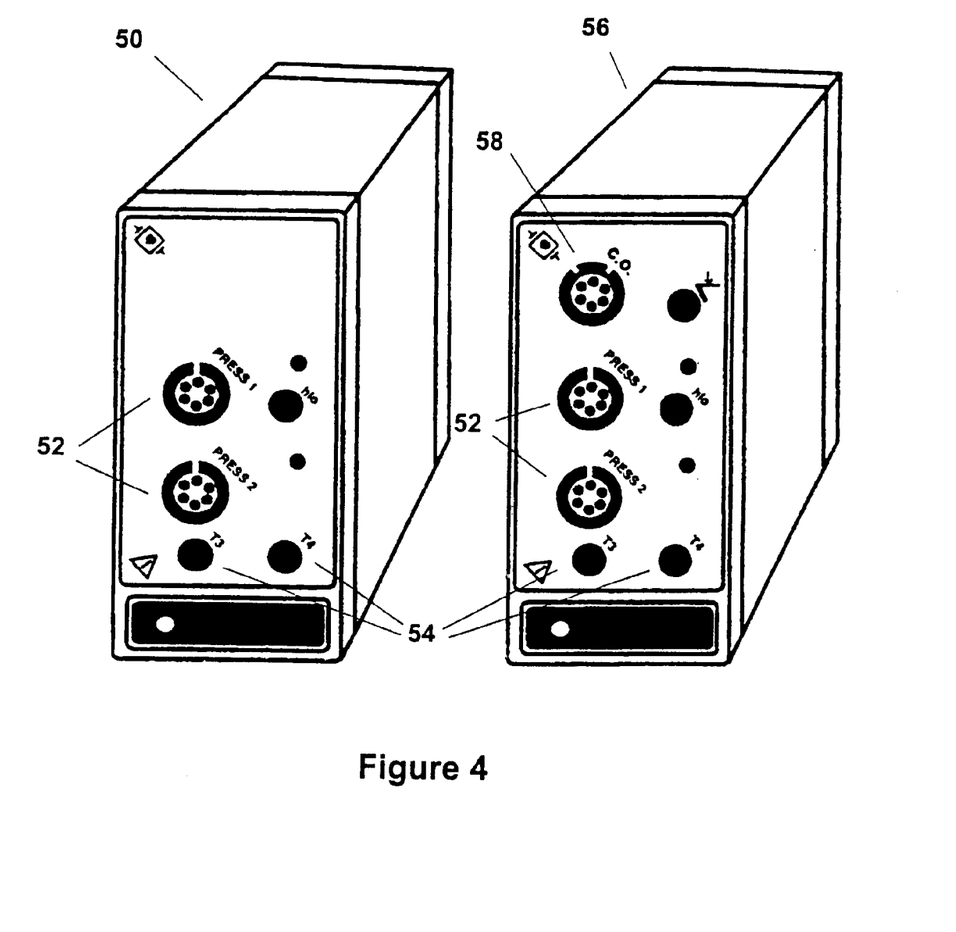
FIG. 4 is an illustration depicting two typical modules that plug in to hospital monitors.

With this in mind, the present invention applies calibrated, real-time pressure signals from the IHM to a circuit that mimics the Abbott Transpac IV circuit (see FIG. 4). The resultant pressure signal to the bedside monitor is compatible with the input characteristics of this commercial device.

The present invention makes use of an IHM system that determines the hemodynamic status of a patient from measurements of estimated pulmonary arterial diastolic pressure and right ventricular pressure obtained from a single absolute pressure sensor implanted in the right ventricle. Both of these measurements have been shown to correlate with the degree of cardiac failure of a patient. The IHM system continually monitors the right ventricular pressure using an absolute pressure sensor and marks the right ventricular pressure at the moment of specific events.

The IHM system may be used in clinical indications that require the measurement of hemodynamic status and, includes but is not limited to, in the diagnosis of the severity of congestive heart failure, pulmonary artery disease, and pulmonary hypertension or the measurement of hemodynamic variables like vascular resistance, contractility, etc. For example, the maximum dP/dt signal derivation capability of the IHM system can also approximate contractility; and the RV diastolic pressure in combination with mean arterial pressure (e.g. measured by a cuff) and a separate measure of cardiac output (measured either invasively or noninvasively) to provide a measure of vascular resistance.

The present invention provides an apparatus and method to enable physicians to view pressure curves available via real-time telemetry, other than by using the programmer. Under current practice, the physician uses a programmer to view the real-time pressure wave along with the EGM tracing. Using the present invention, the IHM system will be able to telemeter real-time signals to any one of a large number of standard monitoring devices. Modules already exist in these sensing devices for monitoring pressure. These modules are routinely used coupled to another signal source, such as a pressure transducer. The present invention is implemented to provide a bridge between the RF telemetered, real-time signal produced by the IHM system and convert that signal to one that approximates the signal these monitoring devices receive from a standard pressure transducer.

Generally, patients will have a standard monitoring system at a bedside for noninvasive monitoring. The IHM system provides a pressure signal comparable to a commercially available catheter. Detecting the signal from the implanted IHM system may be accomplished via several means such as, for example, a lightweight rubber antenna. This antenna may be attached to the patient's clothing or draped over the patient's shoulder, and is then connected to a small telemetry/signal-conditioning box dedicated to this function. The box is then connected to the interface disclosed in the present invention and then to the bedside monitoring device via a standard cable.

Extra-corporeal pressure transducers have been standardized so that many bedside monitors work with several manufacturers' pressure transducers. The circuitry driving the transducers has also been standardized. Accordingly, an interface can be fabricated that mimics the pressure transducer's signals. The interface should also function in cooperation with many standard monitoring systems/devices. The present invention enables these and many other features to enable reliable and continuous remote monitoring of patients while minimizing health care costs.

DETAILED DESCRIPTION OF THE DRAWINGS

Figure 1:
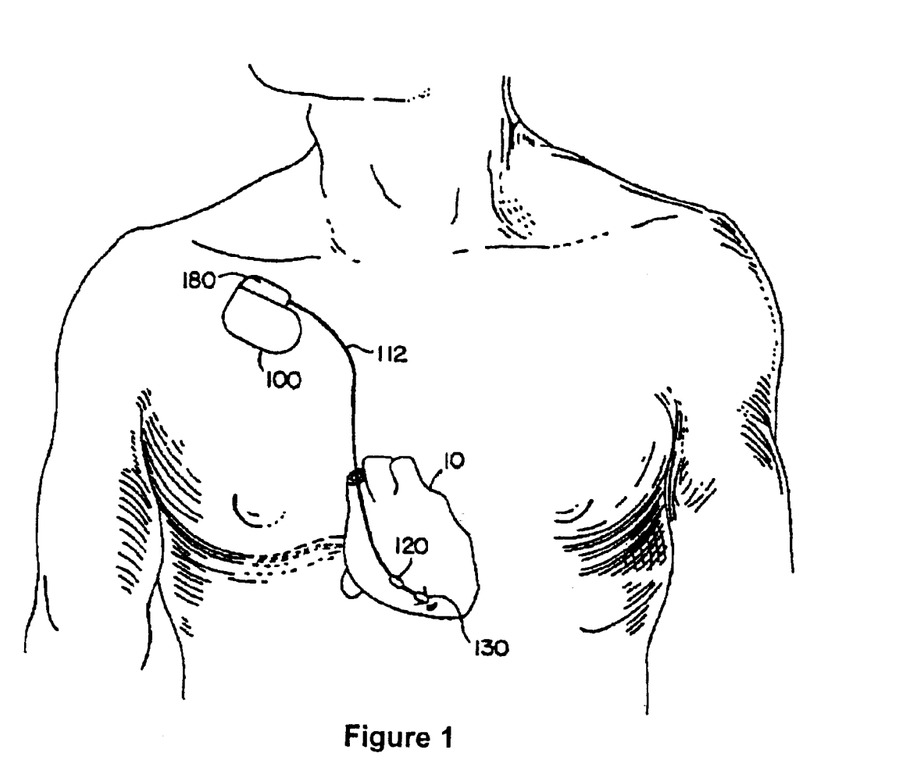
FIG. 1 shows a diagram illustrating an implantable medical device that incorporates an absolute cardiac blood pressure sensor.

FIG. 1 is a diagram representing a patient in whom an implantable medical device that incorporates an absolute cardiac blood pressure sensor has been implanted. Specifically, IMD/IHM 100 is shown coupled to an absolute cardiac blood pressure sensor 120 in a patient's heart 10 for recording absolute blood pressure values. IMD 100 is implanted subcutaneously in the patient's chest region, and it is coupled at its connector module 180 to a lead 112 extending through blood vessels into the right ventricle of the patient's heart 10.

The blood pressure sensor 120 is located on lead 112 just proximal to the lead's distal tip 130 for passively fixing it in position to accommodate continuous movement of the heart 10. In this invention, lead 112 and blood pressure sensor 120 correspond to those disclosed in detail in the above-incorporated, commonly assigned, '434 and '752 patents for deriving absolute blood pressure.

IMD 100 that monitors a physiologic condition or state is programmable and/or can be interrogated by an external programmer or similar instrument through the use of bi-directional RF telemetry that exchanges data and commands via uplink and downlink RF telemetry transmissions through the patient's skin. In the context of an implantable blood pressure monitor, a series of absolute blood pressure signal values are sensed periodically or in response to a signal provided by hospital personnel, e.g., a telemetry downlink signal to initiate real-time data transmission. The absolute blood pressure value signals are continuously transmitted via the present invention so that a physician, clinician, nurse, or other medical expert can determine the status of the patient's cardiac pressures and associate any episode recorded with the time of day.

The physician uses the external programmer to generate and transmit an interrogation command via a downlink telemetry transmission to the IMD 100. IMD 100 recognizes the command and initiates a continuous uplink telemetry transmission of the absolute pressure data in response. The uplink telemetry continues until the IMD system fails to detect further commands. The absolute pressure data is transmitted to a dedicated universal interface (that is the subject of the present invention) and the signal is transmitted and processed as described below in FIGS. 2 and 3.

Figure 2:
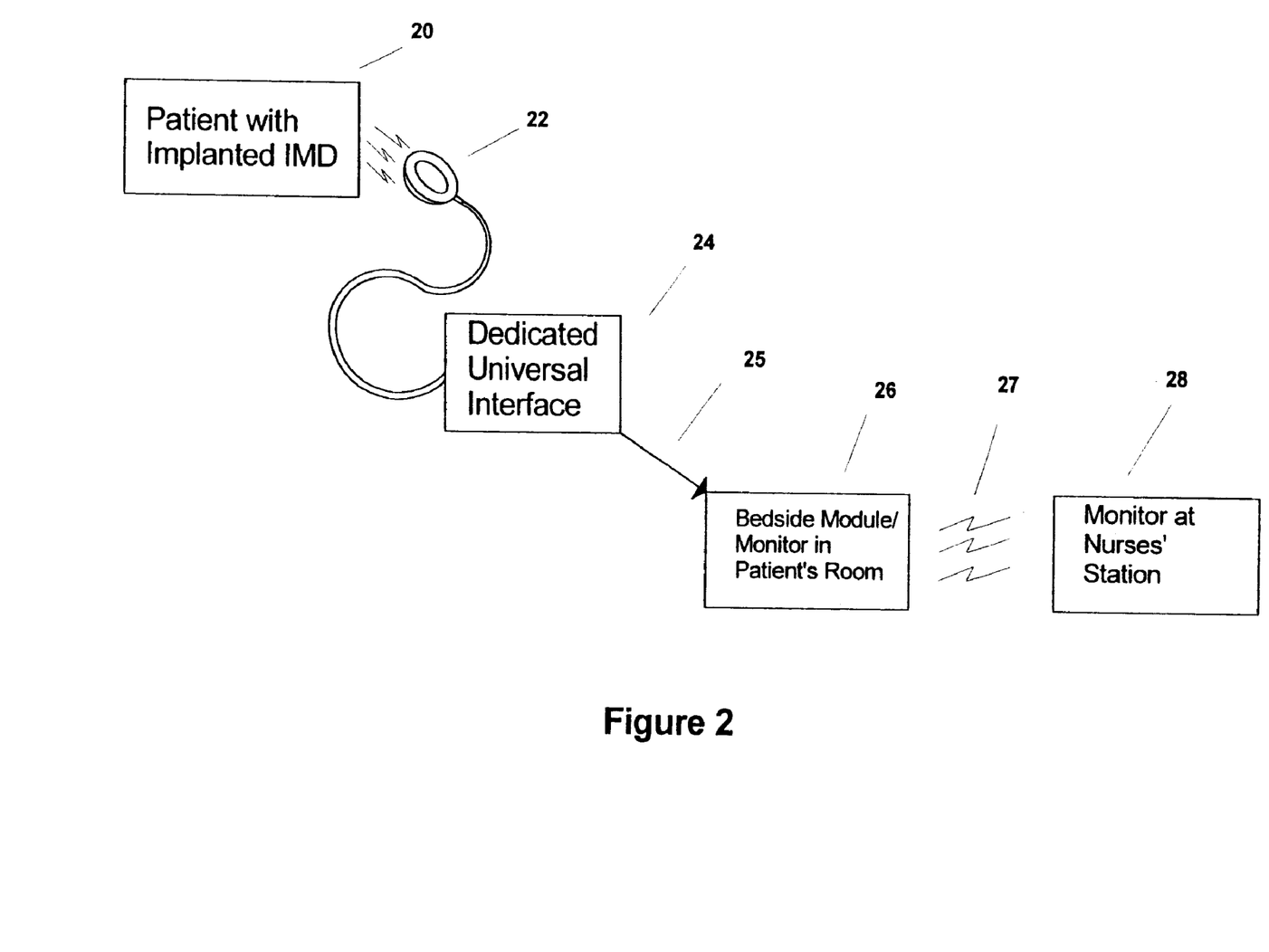
FIG. 2 is a block diagram illustrating the various systems within which the present invention is incorporated.

FIG. 2 illustrates the various systems within which the present invention is incorporated and serves as a bridge from the patient to the hospital's monitoring system. Typically, many patients will require a hospital stay due to the progression of their congestive heart failure. In such instances, it has become apparent there is a need to continuously monitor the patient's cardiac pressure. Accordingly, it is necessary to have the hospital's monitoring system acquire the pressure signals from the IMD. These signals must be translated so that the bedside monitor can display the numbers corresponding to the systolic and diastolic pressures on a continuous and updateable basis. Also, ePAD (a precise, beat-to-beat voltage value) is transmitted to the hospital's monitor. The hospital's monitor may be set up to display "mean" pressure, while the numerical value is ePAD. In addition, these same signals must be capable of being transmitted to a remotely located expert station. The present invention is adaptable to and compatible with built-in capability in a hospital's monitoring system.

Referring now to FIG. 2 in more detail, a heart failure patient with an implanted IMD in a hospital bed 20 is shown. At some time in the past, perhaps upon admission to the hospital, the physician has turned the universal interface On and placed light telemetry head 22 over the implanted system to begin transmission of the blood pressure signals. Further, telemetry head 20 looks up the implanted device's serial number and calibrates the uplinked raw data accordingly. These signals are transmitted to dedicated universal interface 24. Dedicated universal interface 24 operates to convert these signals and transmit them via a standard commercially available telemetry cable 25 to bedside monitor 26. From bedside monitor 26, the signal is telemetered via standard hospital data transfer system 27 connected to an expert station 28 located at a central nurses'station or elsewhere in the hospital.

Figure 3:
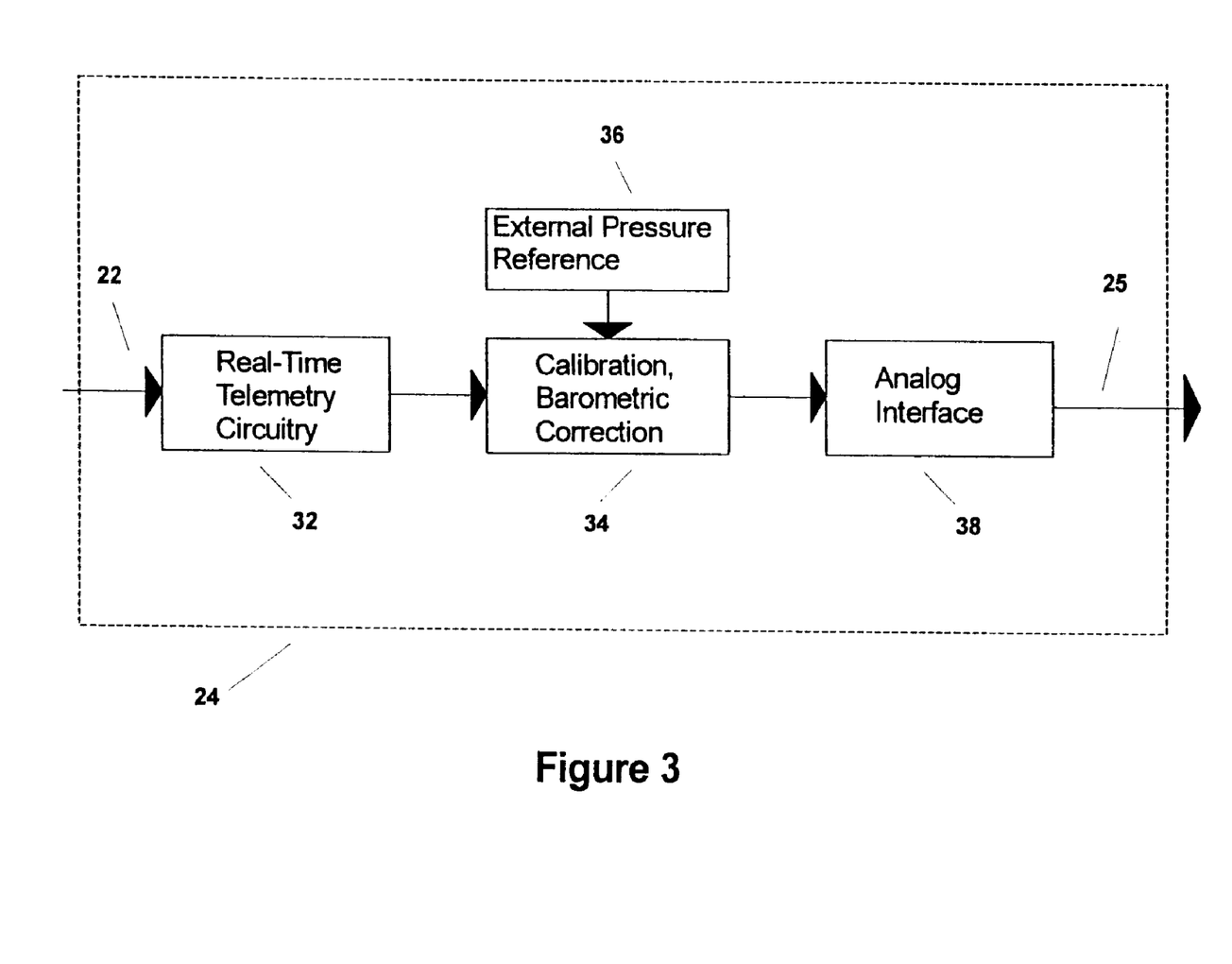
FIG. 3 is a block diagram that illustrates how the absolute blood pressure signal is converted for use by the bedside monitor and the remote expert station in the hospital.

FIG. 3 is a block diagram that illustrates how real-time telemetry and signal conditioning within universal interface 24 is accomplished to generate a signal for use by bedside monitor 26 as well as hospital's remote expert station 28. The RF telemetry signal from the IMD is transmitted to dedicated universal interface 24 via the cable from lightweight telemetry head 22. This signal is transferred to real-time telemetry circuitry 32 whose purpose is to extract the digital signal information. These digital signals are then passed on through calibration and barometric correction means 34.

Certain of the measured physiologic signals derived from the heart or blood in the circulatory system are affected by ambient conditions that cannot be separately measured by the IHDs and physiologic sensors. Specifically, blood pressure and temperature signal values derived by a wholly implantable system are affected by atmospheric pressure acting on the patient and ambient temperature, i.e. a fever afflicting the patient, respectively.

Changes in ambient conditions other than weather changes can also influence the measurement of absolute blood pressure changes. Specifically, either mean or average blood pressure and changes may effect by implantable pressure sensors' readings. For example, when a patient with such an implantable blood pressure sensing medical device changes elevation by ascending or descending in an elevator of a tall building or in an airplane, the change in barometric pressure affects the absolute blood pressure sensed in the body by an amount sufficient to mask physiologic changes. The barometric pressure may also contribute to serious malfunction. This is particularly critical to the operating and detection functions of IHMs which rely on accurately sensing cardiac blood pressure changes that reflect a cardiac function or generate signals consistent with the requirement for cardiac output.

There are several challenges associated with measurement of absolute pressure sensors implemented to measure blood pressure in a heart chamber or blood vessel. Some of these are covered in the above-incorporated, commonly assigned, '752 and '434 patents Specifically, the patents disclose an external pressure recorder that records and time stamps recordings of barometric pressure. It is understood that the recordings are retrieved and used as reference pressure data for comparison with internally recorded absolute blood pressure data.

External pressure reference 36 develops a usable absolute barometric pressure signal that can be combined with the absolute physiologic signal value to derive an accurate physiologic signal value referenced to atmospheric pressure. In this embodiment, the sensor is a barometric pressure reference constructed in the manner described in detail in the above incorporated, commonly assigned, '434 and '752 patents having a diaphragm (not shown) that deflects with changes in absolute barometric pressure. The reference develops signals that are decoded as reference values in an reference signal demodulator that is also described in detail in the above-incorporated '434 and '752 patents. Such external pressure reference 36 is used in the present invention to derive the pressure values. Preferably, the pressure values are referenced to atmospheric pressure, that are routed to analog interface 38 for transmission to bedside monitor via cable 25. Pressure cable 25 transmits a 4 to 10 VDC or RMS AC signal up to 5 KHz to a typical monitor.

Communication from the EPR element could be 1) contained within the unit, 2) hard-wired, 3) via an infrared port, or 4) any standard connector.

FIG. 4 illustrates two modules 50 and 56 that plug into a hospital monitor and are typical of those that are available to and used by hospitals. Preferably the modules are located adjacent to the patient's bed. Module 50 differs from module 56 in that module 50 is able to pass on only cardiac pressures 52 and temperatures 54, whereas module 56 has the additional capability of hosting cardiac output 58. Pressure cable 40 may be attached to bedside module 50 or 56 in receptacles 52 provided. The signals are then decoded into standard format for display, that is, readouts of the systolic and diastolic pressures. Waveforms (RV pressure), where applicable, are also displayed. In addition, the bedside monitor is adapted for connection to the hospital's monitoring network 27. Accordingly, signals may be transmitted to a nearby or remote expert station 28 for observation, interpretation, diagnosis and chronic patient management.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A universal interface for an IMD data management to enable physiologic data transfer from the IMD to hospital systems via various built-in monitoring equipment, the universal interface comprising:

a telemetry circuitry in communication with and configured to receive hemodynamic pressure data from the IMD;

means for calibration of the hemodynamic pressure data with ambient barometric pressure; and means for transmitting the calibrated hemodynamic pressure data from the universal interface to an external hospital monitor in a data format compatible with the external hospital monitor.

2. The universal interface of claim 1, wherein said means for calibration includes an external pressure reference.

3. The universal interface of claim 1, wherein said telemetry circuitry includes wireless communications with the IMD.

4. The universal interface of claim 1, wherein the external hospital monitor is a bedside monitor.

5. The interface of claim 1, wherein the data format corresponds to an Abbot Critical Care Transpac IV format.

6. A medical data transfer and exchange system including an IHM/IMD, wherein a universal interface connects the system to a network of hospital monitors comprising:

a telemetry system to wirelessly retrieve the medical data from the IHM/IMD;

the universal interface being in data communications with the telemetry system and configured to correlate the medical data to a format; and the network of hospital monitors being in data communications with the IHM/IMD via said universal interface, wherein the universal interface transmits the medial data to the network in date format compatible with the network.

7. The system of claim 6, wherein said universal interface includes a telemetry circuitry.

8. The system of claim 6, wherein said universal interface includes means for calibration of barometric pressure.

9. The system of claim 6, wherein said universal interface includes an analog interface adapted to connect to the network of hospital monitors.

10. The system of claim 6, wherein said universal interface includes said network of hospital monitors which includes equipment manufactured by various manufacturers.

11. The system of claim 10, wherein said equipment includes various connection and porting standards.

12. The system of claim 6, wherein said network of hospital monitors includes bedside modules located proximate to a patient or in a patient's room.

13. The system of claim 6, wherein the data format corresponds to an Abbot Critical Care Transpac IV format.

14. A universal system for acquiring physiologic signals from an IMD/IHM and transmitting the signals to one or more monitoring devices distributed in a hospital monitoring network, the system in continuation with the network comprising:

a physiologic signal originating from the IMD/IHM;

means for retrieving the physiologic signals; and means for conditioning the signals for transmission to said one or more monitoring devices.

15. The system of claim 14, wherein said means for retrieving includes a telemetry circuitry.

16. The system of claim 14, wherein said means for conditioning the signals includes a universal interface.

17. The system of claim 14, wherein said one or more monitoring devices include a variety of modules made by various manufacturers.

18. The system of claim 14, wherein the means for conditioning include formatting the signal into a format compatible with an Abbot Critical Care Transpac IV format.

* * * * *

UNITED STATES PATENT AND TRADEMARK OFFICE
CERTIFICATE OF CORRECTION

PATENT NO. : 6,650,939 B2 Page 1 of 1
APPLICATION NO. : 09/809914
DATED : November 18, 2003
INVENTOR(S) : Robert T. Taepke et al.

It is certified that error appears in the above-identified patent and that said Letters Patent is hereby corrected as shown below:

Column 8, line 44, please delete "in date format" and insert --in data format--

Signed and Sealed this

Nineteenth Day of December, 2006

JON W. DUDAS
*Director of the United States Patent and Trademark Office*